United States Patent [19]
Hughes

[11] Patent Number: 5,619,042
[45] Date of Patent: Apr. 8, 1997

[54] SYSTEM AND METHOD FOR REGULATING DELIVERED RADIATION IN A RADIATION-EMITTING DEVICE

[75] Inventor: John H. Hughes, Martinez, Calif.

[73] Assignee: Siemens Medical Systems, Inc., Iselin, N.J.

[21] Appl. No.: 504,724

[22] Filed: Jul. 20, 1995

[51] Int. Cl.⁶ ............................. H05G 1/44; G21K 1/04; H01J 37/244
[52] U.S. Cl. .................... 250/492.3; 250/252.1; 250/492.1; 378/109; 378/150
[58] Field of Search ................... 250/492.1, 492.3, 250/505.1, 252.1; 378/108, 150

[56] References Cited

U.S. PATENT DOCUMENTS

| | | | |
|---|---|---|---|
| 3,777,124 | 12/1973 | Pavkocich | 378/117 |
| 3,783,252 | 1/1974 | Pavkovich | 378/117 |
| 4,028,544 | 6/1977 | Hounsfield | 250/252 |
| 4,044,260 | 8/1977 | Housnsfield | 250/360 |
| 4,639,943 | 1/1987 | Heinze | 378/108 |
| 4,748,696 | 5/1988 | Griesmer et al. | 378/108 |
| 4,823,370 | 4/1989 | Kikuchi | 378/99 |
| 4,916,722 | 4/1990 | Ema | 378/99 |
| 5,050,196 | 9/1991 | Kadosawa et al. | 378/108 |
| 5,148,032 | 9/1992 | Hernandez | 250/492.1 |
| 5,216,255 | 6/1993 | Weidlich | 250/505.1 |
| 5,267,296 | 11/1993 | Strommer | 378/108 |

OTHER PUBLICATIONS

Faiz M. Khan, Ph.D., "The Physics of Radiation Therapy", 2d ed., pp. 200–206.
Siemens Product Brochure, "Digital Systems for Radiation Oncology", pp. 1–16.

Primary Examiner—Bruce C. Anderson

[57] ABSTRACT

In a radiation emitting device, particularly in a radiation treatment device, the actual radiation delivered to an object via a radiation beam is adjusted dependent on the dimensions of an opening in a plate arrangement provided between a radiation source and an object so that the radiation output has a constant output factor over an irradiation field, regardless of the size of the opening. The output factor is defined as the ratio of the radiation output in air with a scatterer (such as shielding plates) in the beam path to the radiation output without the scatterer for a reference field.

8 Claims, 3 Drawing Sheets

5,619,042

SYSTEM AND METHOD FOR REGULATING DELIVERED RADIATION IN A RADIATION-EMITTING DEVICE

BACKGROUND OF THE INVENTION

1. Field of the Invention

The invention relates to a radiation-emitting device, and particularly to a system and a method for regulating the radiation delivered to an object in a radiation treatment device.

2. Description of the Related Art

Radiation-emitting devices are generally known and used, for instance as radiation therapy devices for the treatment of patients. A radiation therapy device generally comprises a gantry which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on one zone of a patient lying in the isocenter of the gantry rotation.

In order to control the radiation emitted toward an object, a beam-shielding device such as a plate arrangement or collimator is usually provided in the trajectory of the radiation beam between the radiation source and the object. This beam-shielding device defines a field on the object to which a prescribed amount of radiation is to be delivered.

The radiation delivered to an object may be analyzed into primary and scattered components. The primary radiation is made up of the initial or original photons emitted from the radiation source, and the scattered radiation is the result of the photons scattered by the plate arrangement itself. The beam's radiation output in free space increases because of the increased collimator scatter, which is added to the primary beam. In other words, a point in the field is subjected not only to direct radiation, that is the primary component, but also to radiation that is scattered from the plate arrangement. The ratio of the radiation output in air with the scatterer to the radiation output without the scatterer for a reference field (for instance 10×10 cm) is commonly called the "output factor" or the collimator scatter factor. The concept and definition of the output factor are well understood in the art.

Thus, due to these scattered photons, the dose rate applied to the surface of the object changes dependent on the size of the opening in the plate arrangement, that is, on the field size. This means that the radiation emitted to the same spot, for instance in the center of the radiation beam onto the object, changes according to the size of the opening in the plate arrangement. When the plate arrangement shows only a small opening, then the accumulated dose at the same spot is less than the accumulated dose at the same spot when the opening is big.

The delivery of radiation by such a radiation therapy device is prescribed and approved by an oncologist. Actual operation of the radiation equipment, however, is normally done by a therapist. When the therapist administers the actual delivery of the radiation treatment as prescribed by the oncologist, the device is programmed to deliver that specific treatment. When programming the treatment, the therapist has to take into consideration the output factor and has to adjust the dose delivery based on the plate arrangement opening in order to achieve the prescribed radiation output on the surface of the object. This adjustment can be made according to known calculations, but the therapist normally has to do them manually, which can easily lead to errors. In the context of radiation therapy, a miscalculation can lead to either a dose that is too low and is ineffective, or that is too high and dangerous; a large error, for example, a misplaced decimal point, can be lethal.

What is needed is a system that eliminates this significant source of errors, a system that automatically adjusts the delivery of radiation to the object in order to make sure that the actually delivered radiation output is exactly the same as the desired radiation output, independent of the shape or size of the opening in the plate arrangement in the trajectory of the radiation beam.

SUMMARY OF THE INVENTION

According to the invention, radiation output delivered to an object from a radiation source, is regulated by generating a radiation beam using a radiation source having a variable radiation output. An irradiated field of the object is defined. The beam is shielded, preferably by an arrangement of at least one movable plate between the radiation source and the object. An output factor of the radiation is thereby varied according to the degree of shielding, in which the output factor is defined as the ratio between a reference radiation output of the beam when unshielded and an actual radiation output of the beam as shielded. The radiation output is varied such that the output factor is constant regardless of the degree of shielding. The output factor is preferably equal to unity.

In one embodiment of the invention, a reference radiation output value is sensed for a reference plate position. Relative radiation output values are then also sensed for each of a plurality of plate positions covering a predetermined range of motion of each movable plate. A series of correction values is then generated as a predetermined comparison function of the reference radiation output value and each of the relative radiation output values. These correction values are stored in a memory. The radiation output is then varied as a predetermined correction function of nominal dose signals and the correction value for each respective plate position of a prescribed treatment profile.

The system may be pre-set by generating a series of calibration signals and field geometry parameters corresponding to a plurality of field sequences of a predetermined treatment. The signals are then downloaded using a verification and auto-set circuit into the memory the series of calibration signals before an actual treatment.

DETAILED DESCRIPTION

The invention is described below with primary reference to a system for delivering X-ray radiation to a field of a patient, and for delimiting the field using at least one movable plate in the beam path from a radiation source. This is by way of example only. The invention may be used to regulate the delivery of any type of energy, for example, electrons (instead of X-rays), to any type of object (not just a human patient), provided the amount of energy delivered to the field can be sensed or estimated.

Figure 1:
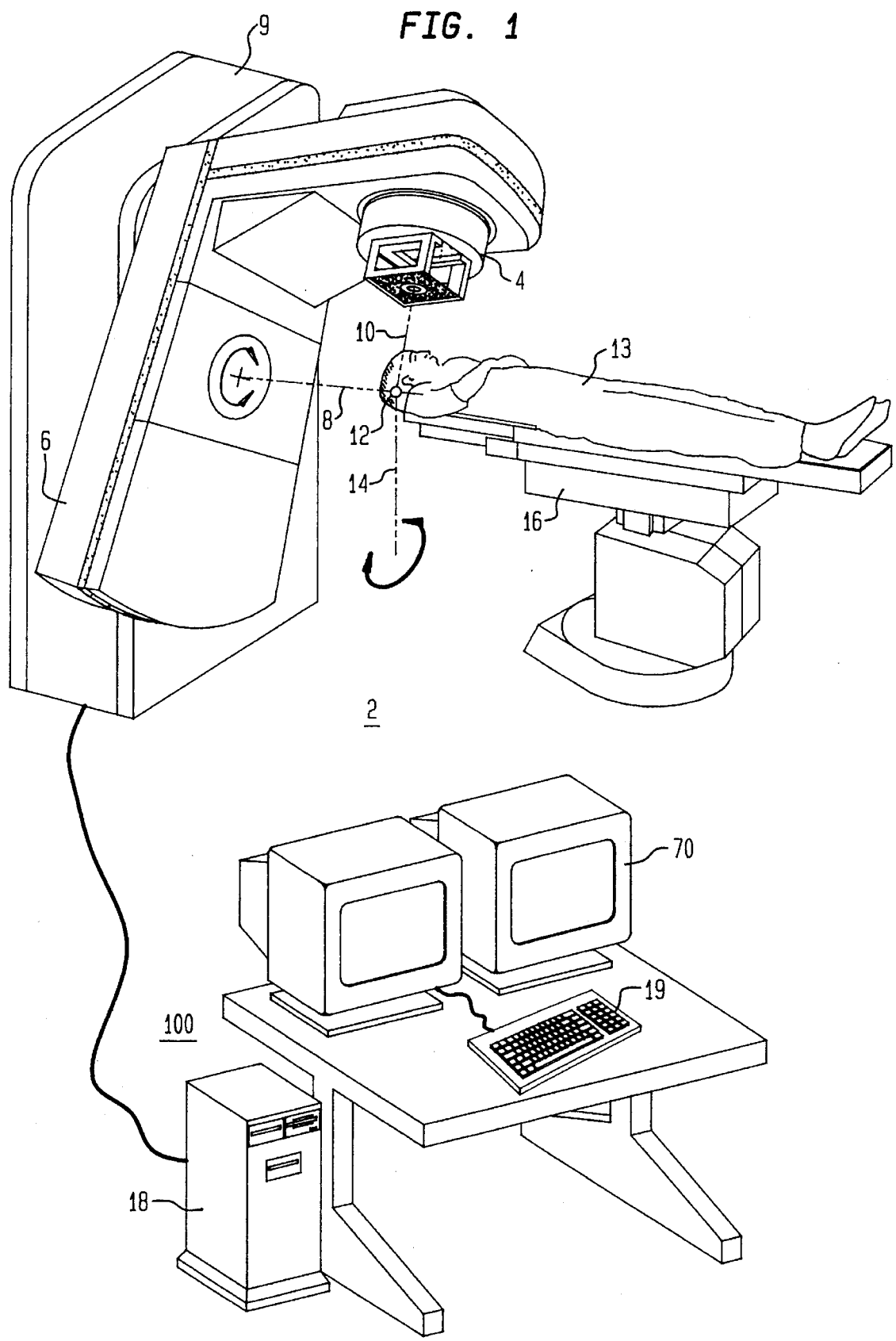
FIG. 1 is a schematic diagram of a radiation treatment device and a treatment unit constructed in accordance with the invention.

FIG. 1 shows a radiation treatment device 2 of common design, in which plates 4 and a control unit in a housing 9 and a treatment unit 100 constructed in accordance with the principles of the invention are used. The radiation treatment device 2 comprises a gantry 6 which can be swiveled around a horizontal axis of rotation 8 in the course of a therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated by 10. Electron, photon, or any other detectable radiation can be used for the therapy.

During the treatment the radiation beam is trained on a zone 12 of an object 13, for example, a patient who is to be treated, and who lies at the isocenter of the gantry rotation. The rotational axis 8 of gantry 6, the rotational axis 14 of a treatment table 16, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

The area of the patient that is irradiated is known as the field. As is well known, the plates 4 are substantially impervious to the emitted radiation. They are mounted between the radiation source and the patient in order to delimit the field. Areas of the body, for example, healthy tissue, are therefore subjected to as little radiation as possible, and preferably to none at all. In the preferred embodiment of the invention, at least one of the plates is movable so that the distribution of radiation over the field need not be uniform (one region can be given a higher dose than another); furthermore the gantry can preferably be rotated so as to allow different beam angles and radiation distributions without having to move the patient around. Neither or these features is necessary according to the invention: the invention may also be used with fixed-field devices (no movable plates), with constant radiation delivery rates, and with fixed-angle beams (no rotatable gantry).

Radiation treatment device 2 also includes a central treatment processing or control unit 100, which is usually located apart from radiation treatment device 2. The radiation treatment device 2 is normally located in a different room to protect the therapist from radiation. Treatment unit 100 includes output devices, such as at least one visual display unit or monitor 70, and an input device such as a keyboard 19, although data can be input also through data carriers, such as data storage devices, or an verification and recording or automatic set-up system 102, which is described below. The treatment processing unit 100 is typically operated by the therapist who administers actual delivery of a radiation treatment as prescribed by an oncologist. By utilizing the keyboard 19, or other input device, the therapist enters into a control unit 76 of the treatment unit 100 the data that defines the radiation to be delivered to the patient, for example, according to the prescription of the oncologist. The program can also be input via another input device like a data storage device, through data transmission, or using the automatic set-up system 102. On the screen of a monitor 70 various data can be displayed before and during the treatment.

Figure 2:
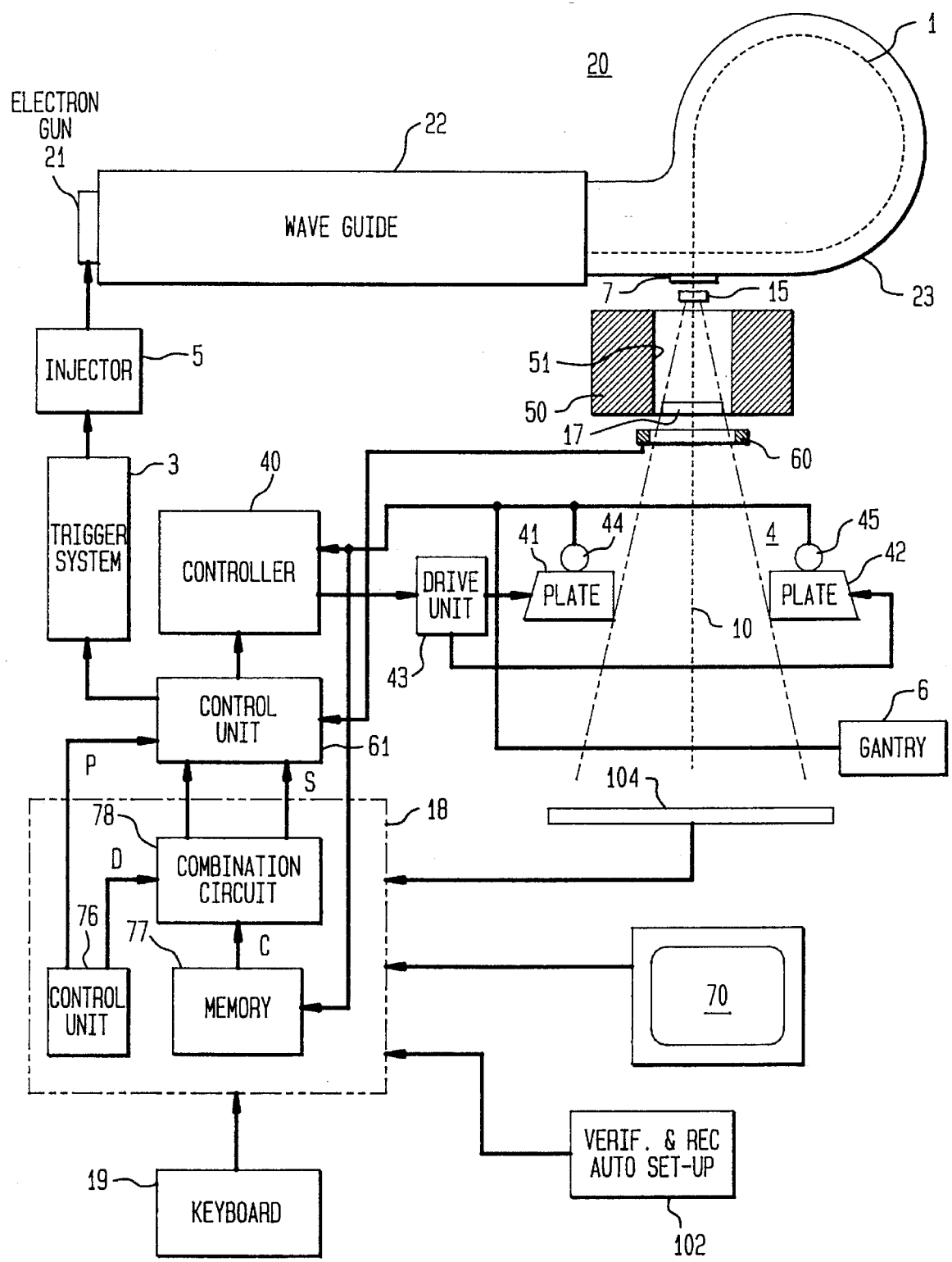
FIG. 2 is a block diagram illustrating portions of a processing unit, a control unit and a beam generation system in the radiation treatment device of FIG. 1.

FIG. 2 shows portions of an illustrative radiation treatment device 2 and portions of treatment unit 100 in more detail. An electron beam 1 is generated in an electron accelerator 20. Accelerator 20 comprises an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the dose is ascertained. If the scattering foils are replaced by a target, the radiation beam is an X-ray beam. Finally, aperture plate arrangement 4 is provided in the path of radiation beam 1, by which the irradiated field of the subject of investigation is determined. Aperture plate arrangement 4 includes a pair of plates 41 and 42. As is described above, this is just one example of a beam-shielding arrangement that can be used in the invention. The invention will work with others also as long as there is an aperture plate arrangement that defines an irradiated field.

Plate arrangement 4 comprises a pair of aperture plates 41 and 42 and an additional pair of aperture plates (not shown) arranged perpendicular to plates 41 and 42. In order to change the size of the irradiated field the aperture plate can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions. This is just one example of such a system. The invention will work with other systems also, as long as there is a beam-shielding arrangement that defines an irradiated field and as long as sensors are provided to indicate the field size.

Motor controller 40 is coupled to a dose control unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, dose control unit 61 supplies signals to trigger system 3, which changes in a known manner the pulse repetition frequency so that the deviation between the set values and the actual values of the radiation beam output is minimized.

In such a radiation treatment device the output of the radiation beam impinging on the surface of an object is dependent on the size of the opening in plate arrangement 4 and thus, on the size of the irradiated field on object 13.

In the following, for the sake of clarity and simplicity only, the invention is described in connection with the additional pair of plates (not shown) being stationary. The invention may be used, however, in systems with additional movable plates, as long as suitable motor controllers and position sensors are provided. When plates 41 and 42 move apart from each other and thus widen the gap in-between, the actually delivered radiation output at any given spot on object 13, for example in the axis 10 of the radiation beam, increases due to the increased scatter, which is added to the primary beam.

In order to make sure that during treatment the radiation output at the same spot on the surface of object 13 always equals the desired radiation output, independent of the size of the opening, the output of the radiation beam must be adjusted according to the opening size.

Central processing unit 18 is connected, on the one hand, with the input device, such as the keyboard 19, for inputting the prescribed delivery of the radiation treatment and, on the other hand, with a dose control unit 61 that generates the desired values of radiation for the controlling trigger system 3. Trigger system 3 then adapts the pulse repetition frequency or other parameters in a corresponding, conventional manner. The ability to change the radiation output is generally known and it is particularly advantageous to use a digital dosimetry system because then it can easily be controlled by the digital output of central processing unit 18.

Figure 3:
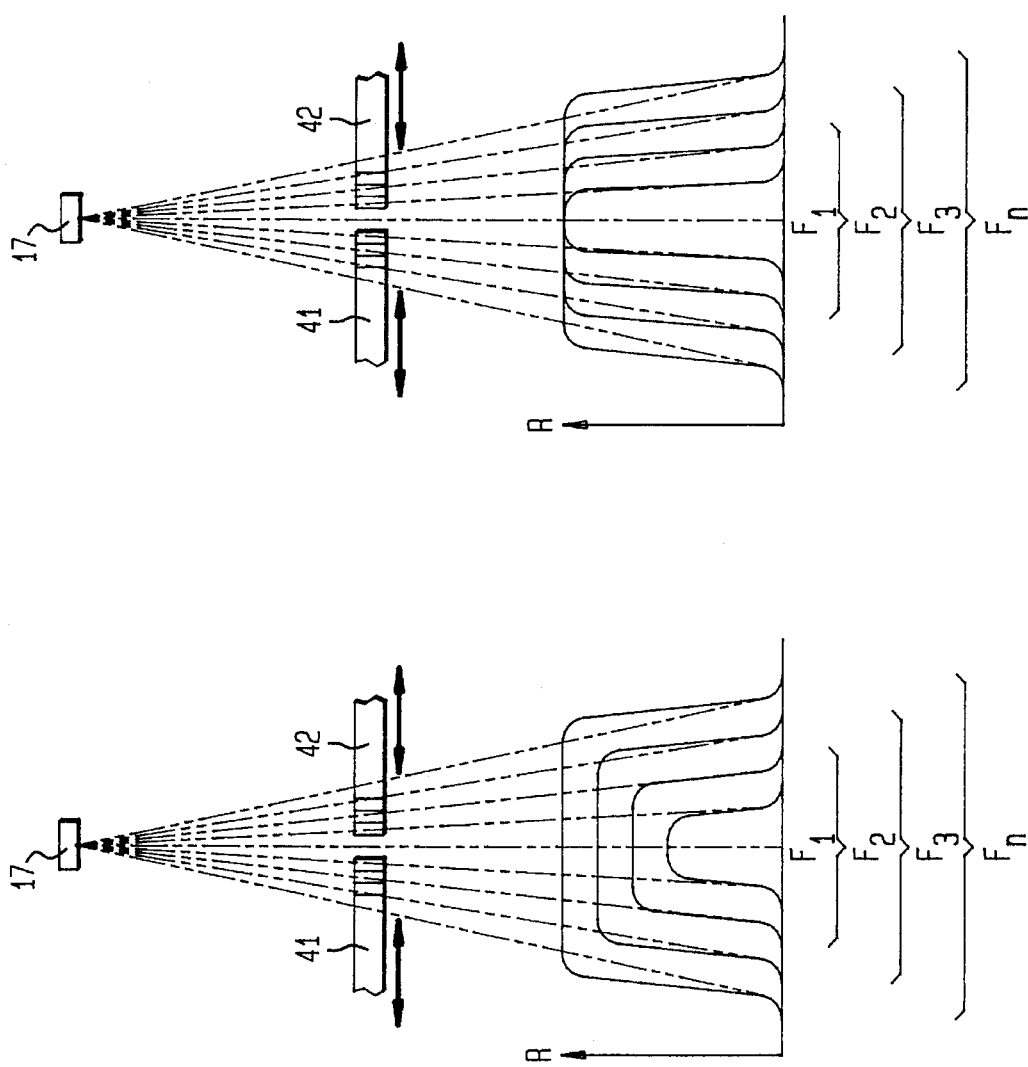
FIG. 3 shows the radiation output delivered from a radiation source to various field sizes on an object according to the prior art.

FIG. 3 shows how the radiation output factor R depends on the size of the opening between plates 41 and 42 and thus, on the field sizes F1 to Fn on object 13 according to the prior art. Plates 41 and 42 are movable by drive unit 43 for widening or narrowing the opening, whereas, in this example, the other pair of plates is assumed to be stationary. As is described above, if the radiation output emitted by radiation source 17 is constant, the output factor R will increase as the field size increases from F1 to Fn.

Figure 4:
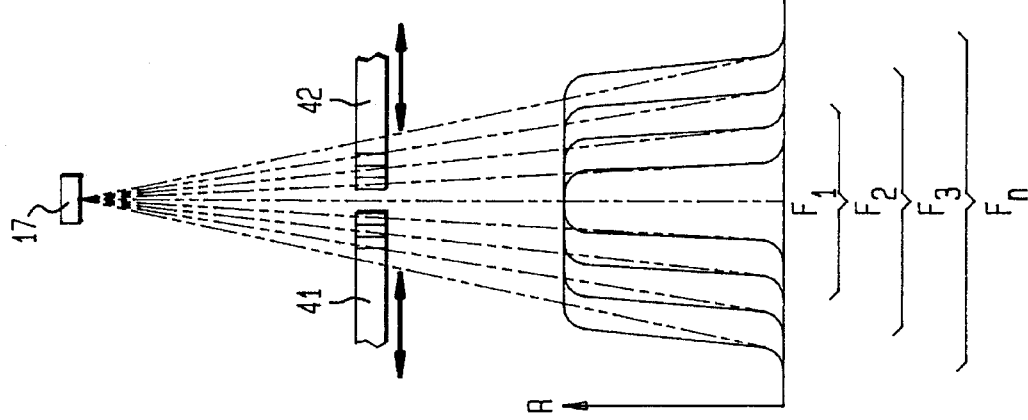
FIG. 4 shows the radiation output delivered from a radiation source to various field sizes on an object according to the invention.

FIG. 4 shows the same configurations of plates 41 and 42, however, according to the invention, in which the radiation output is regulated in such a way that the output factor remains constant despite a changing field size, that is, despite changes in the size of the openings in the plate arrangement 4. To this end, the output signals of position sensors 44 and 45, or any other signals indicative to the size and/or shape of the opening, are applied to central processing unit 18 for providing adjusted dose signals which take into account the size and/or shape of the openings and thus provide a constant output factor R. The radiation output is preferably regulated so that the output factor is kept at R=1 over the full range of motion of the plates during treatment. This implies that the radiation actually delivered is exactly equal to the radiation prescribed, despite a changing field size.

Note that, although the radiation output factor is held constant as the field size increases, this does not mean that the accumulated dose must be constant over the field. In fact, the reason for changing the field size at all during a treatment is normally to create a non-uniform pattern of radiation delivery over the field; for example, a wedge-shaped accumulated dose profile may be prescribed to deliver more radiation to an area of a tumor while avoiding adjacent healthy tissue. In FIG. 4, for example, the accumulated dose in field F1 will be greater than the accumulated dose in the region between field F2 and F3. What the invention provides is a way to make sure that radiation output is precisely regulated to eliminate the uncertainty introduced by scattering, that is, because of the output factor. Even more complicated profiles can be achieved by rotating the gantry as well as changing the field size.

Central processing unit 18 includes control unit 76 which controls the execution of the program and which supplies position signals P for controlling the opening of plate arrangement 4 and nominal dose signals D (corresponding to the plate position that would be demanded using prior art methods, that is, without regard to output factor compensation) for adjusting the radiation output at the output of radiation source 17. A memory 77 is also provided in or is connected to the central processing unit 18 for supplying correction signals C, which the processing unit uses to adjust the radiation output dependent on the position signals P supplied from position sensors 44 and 45 in order to achieve the predetermined constant output factor.

The preferred arrangement of the memory unit is that, for each plate position (field size), it has stored a corresponding dose correction signal C. The memory thus stores a table of correction factors. If more than one set of movable plates is included in the system, then the table will be correspondingly multi-dimensional, and arranged using any known data structure, so that a correction factor is available for any combination of plate positions.

Control unit 76 and memory 77 apply the dose and correction signals D and C, respectively, to a combination circuit 78, which combines the values to generate set signals S. The set signals S are in turn applied to the dose control unit 61, which sets the radiation output.

The combination circuit 78 will depend on the form in which the correction signals are generated and stored. Assume that the correction signals C are stored as additive offset. In this case, the combination circuit will be an adder which adds the correction signals C to dose signals D. This is the preferred embodiment, since it is simplest. If, however, the correction factors are multipliers (for example, an increase in radiation output by a factor of 102/100 would require a multiplicative correction signal of 100/102. Instead of storing actual values of the correction signals C, it is also possible to store the parameters of a correction function for the various each field sizes. The processing unit would then evaluate the function for each current field size using the parameters stored in the memory, and would then generate the correction signals (additive or multiplicative) itself.

The correction signals are determined before actual treatment of a patient in one or more calibration runs. To determine relative correction values, a reference surface (or line) is irradiated with a known reference plate position, and the radiation output over the surface is sensed by a conventional sensing device 104 (see FIG. 2), which generates radiation output signals that are applied to the processing unit 18. The reference surface need not lie in the patient plane, although if it does the calibration will typically be easier and more accurate. Note that the radiation output may be sensed and stored for several different points of the surface, since the output may not be constant.

The plates are then moved to a new opening position, the radiation output is sensed and stored, and so on, until radiation output values are stored for the reference surface over the entire range of motion of the plates. If more than one set of movable plates is included, then calibration output values will be sensed and stored for each combination of plate positions; the number of combinations will depend on the desired or required resolution.

Once a complete set of calibration output values is stored, each value is compared with the value for the reference plate position (the reference output value). If additive offsets are chosen for the correction factors, then the difference between the sensed output values and the reference output value is stored. If multiplicative correction factors are chosen, then ratios are stored. Alternatively, any known function approximation method may be used to generate the parameters of an approximating function of the additive or multiplicative correction factors required.

Note that the correction factors obtained in the calibration steps just described will lead to a constant output factor, but not necessarily an output factor R=1. This is because the reference plate position itself may cause scattering, so that the reference radiation output value will not be equal to a known absolute radiation output value. In order to correct for this, one should preferably choose as the sensing device 104 a device that is able to measure actual absolute radiation output, or one should use another conventional device to obtain an absolute output value for at least one plate position, which then is used as the reference plate position. In order to ensure accuracy over time, recalibration runs may be carried out, and new correction factors calculated and stored, according to a predetermined calibration schedule.

The output sensing device does not have to directly measure the absolute output. Rather, it may measure dose rates for different plate positions, which will yield output values using known integration and offset techniques.

Figure 5:
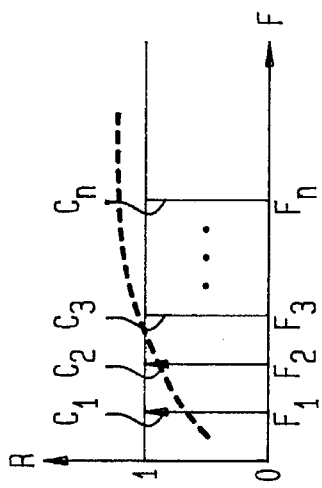
FIG. 5 shows a diagram of output factors versus the sizes of an rectangular field on an object, in which one dimension of the field is held constant.

FIG. 5 shows a diagram indicating in a solid line a constant output factor R=1 which is achieved according to the invention, and in dashed lines, an output factor according to the prior art. The horizontal axis shows one parameter of the field size F defined by plate arrangement 4 and the vertical axis shows the output factors R. The differences between the lines indicate the values of the correction signals C1 to Cn for different field sizes F1 to Fn.

The invention makes it possible to adjust the output factor R, preferably to R=1, which means that if an oncologist advises a therapist to deliver a certain radiation output, the therapist does not have to take into account the respective output factor R. Then, the radiation treatment device automatically adjusts the radiation output according to the dimensions of the field. This reduces or wholly eliminates the errors induced when the therapist must calculated and compensate for variations in the output factor.

The invention can also be carried out in a radiation therapy device in which at least one aperture plate of plate arrangement 4 is movable during treatment. Such a device is described in U.S. Pat. No. 5,148,032. As described in this U.S. Patent, in such a radiation treatment device, various isodose curves can be easily achieved without a physical wedge being present in the trajectory of the beam. In this case also the correction values are added to the radiation output values to achieve a given output factor. Similar corrections may be used in devices that use a physical wedge. In either case, corresponding correction values C can be applied to the dose signals D in order to achieve a correct delivery of radiation to the object.

A "course" of radiation treatment may, and often does, have more than one field, and may run over several different sessions. In some cases, hundreds of different (and, in some cases, fixed) sequential fields are used during a course, for example, to provide proper irradiation of a field that has a complicated geometry or prescribed dose profile, to lessen discomfort to the patient, or to adjust the field as a tumor shrinks during treatment. The invention therefore also comprises an optional verification and recording or "auto set-up" system 102 (see FIG. 2), which stores and downloads to the radiation system (via the CPU 18 or directly into the memory) the parameters, for example, of the geometry, of the various fields of the course of treatment, and/or the tables of correction factors that were derived during earlier calibration runs for the various fields.

I claim:

1. A method for regulating the radiation output delivered to an object from a radiation source, comprising the following steps:

generating a radiation beam having a variable radiation output;

defining an irradiated field of the object;

varying a degree of shielding of the beam, an output factor of the radiation output thereby varying according to the degree of shielding, in which the output factor is defined as the ratio between a reference radiation output of the beam when unshielded and an actual radiation output of the beam as shielded; and varying the radiation output such that the output factor is constant regardless of the degree of shielding.

2. A method as in claim 1, in which the output factor is equal to unity.

3. A method as in claim 1, in which the step of varying the degree of shielding of the beam comprises the step of moving at least one movable shielding plate located between the radiation source and the object.

4. A method as in claim 3, further including the following steps:

sensing a reference radiation output value for a reference plate position;

sensing a relative radiation output values for each of a plurality of plate positions covering a predetermined range of motion of each movable plate;

generating a series of correction values as a predetermined comparison function of the reference radiation output value and each of the relative radiation output values;

storing in a memory the series of correction values;

varying the radiation output as a predetermined correction function of nominal dose signals and the correction value for each respective plate position of a prescribed treatment profile.

5. A method as in claim 4, further including the following steps:

generating a series of calibration signals and field geometry parameters corresponding to a plurality of field sequences of a predetermined treatment; and downloading into the memory the series of calibration signals before an actual treatment.

6. A system for regulating the radiation output delivered to an object from a radiation source, comprising:

a radiation source generating a radiation beam having a variable radiation output;

an irradiated field of the object;

beam-shielding means for delimiting the output beam to at least one predetermined irradiation field of the object;

sensing means for sensing radiation output of the shielded output beam and for generating radiation output signals corresponding to radiation output delivered to predetermined portions of the field;

a dose controller for varying a degree of shielding of the beam; and processing means for generating and applying to the dose controller set dose signals, comprising nominal dose signals and dose correction factors, and for thereby varying the radiation output such that an output factor is constant regardless of the degree of shielding, where the output factor is defined as a ratio between a reference radiation output of the beam when unshielded and an actual radiation output of the beam as shielded.

7. A system as in claim 6, in which the output factor is equal to unity.

8. A system as in claim 6, in which the beam-shielding means comprises at least one movable shielding plate located between the radiation source and the object.

* * * * *